United States Patent [19]

Okada et al.

[11] 4,102,177

[45] Jul. 25, 1978

[54] DENSITOMETER

[75] Inventors: Mitsuyoshi Okada, Yokohama; Tetsuya Okuno, Chofu; Takehiko Sato, Yokohama; Masao Shima, Tokyo, all of Japan

[73] Assignee: Yamatake-Honeywell Co., Ltd., Tokyo, Japan

[21] Appl. No.: 784,281

[22] Filed: Apr. 4, 1977

[30] Foreign Application Priority Data

Nov. 12, 1976 [JP] Japan ................... 51-136726

[51] Int. Cl.² ..................... G01N 9/24; G01N 21/06
[52] U.S. Cl. .......................... 73/32 R; 73/61.1 R; 250/575; 356/208
[58] Field of Search .......... 73/32 R, 53, 61 R, 61.1 R; 356/208; 250/564, 573, 574, 575, 576; 259/DIG. 44

[56] References Cited

U.S. PATENT DOCUMENTS

| 3,478,578 | 11/1969 | Dukek et al. | 73/61.1 R |
| 3,899,688 | 8/1975 | Perieres | 356/208 |

FOREIGN PATENT DOCUMENTS

1,440,558 6/1976 United Kingdom .............. 356/208

Primary Examiner—Richard C. Queisser
Assistant Examiner—Stephen A. Kreitman
Attorney, Agent, or Firm—Laurence J. Marhoefer

[57] ABSTRACT

A densitometer for measuring a concentration of matter in a fluid system comprised of liquids and suspended and/or floating matter such as, for example, a densitometer for measuring the concentration of oil in bilge water that includes suspended and/or floating solid material. Two emulsifying conditions of the system are produced by first emulsification with a relatively high power emulsifying action and then a relatively low power emulsification. The amount of light which penetrates the system is a function of the turbidity which varies with the intensity of the emulsification. The concentration of oil in water, for example, in bilge water, is a function of the ratio of the amount of light which passes through the system in the two turbid states.

13 Claims, 10 Drawing Figures

DENSITOMETER

BACKGROUND OF THE INVENTION

1. Field of the Invention

This invention relates to densitometers for optically measuring a concentration of liquid or solid in a sample medium and, more particularly, to a densitometer for measuring a concentration of liquid or solid having the property that particle diameters of the liquid or solid being measured are changeable in response to an operation of an emulsifier.

2. Description of the Prior Art

A conventional densitometer for measuring a concentration of a liquid or solid on the basis of the turbidity of a fluid sample passing through an optical cell being measured on the basis of light transmitted through the sample fluid when it is illuminated with monochromatic light or white light has a disadvantage since various particle diameters of the liquid or solid in the sample fluid are dispersed at random therein, and it is, therefore, difficult to precisely measure the concentration via the turbidity of the sample fluid.

In order to avoid such disadvantge, it has been proposed to agitate a sample fluid by means of an ultrasonic wave or a mixer so as to obtain a uniform particle diameter and then optically measure the concentration via the turbidity of the sample fluid.

Such prior art method has encountered a difficult problem when a turbid ingredient produced from suspended solid formed of dust, dirt, etc. is mixed into the sample fluid, thereby involving a measurement error. One attempt has been made to eliminate this problem by measuring a turbid signal of a sample fluid before and after emulsification thereof and then calculating a difference between these two turbid signals thus removing the influence of the suspended solid upon the measurement. However, the turbid signal, which is a function of the detected transmitted light, changes in exponential function, so that it is difficult to remove the influence of the suspended solid upon the measurement by a calculation obtained from the difference between the two turbid signals.

SUMMARY OF THE INVENTION

An object of the invention, therefore, is to provide a densitometer which can calculate a difference between two turbid signals in an extremely easy manner and without having influence of the suspended solid.

Another object of the invention is to provide a densitometer which can precisely measure a concentration of oil contained in bilge produced in a tanker or any other ships or produced in ballast water.

A further object of the invention is to provide a densitometer comprising an optical system for measuring a concentration of a sample fluid by calculating turbid signals of two fluid samples whose degrees of emulsification obtained by an emulsifier are different from each other, thereby obviating influence of irregular particle diameters.

A still further object of the invention is to provide a densitometer comprising a calculation circuit which can derive a value corresponding to true concentration of a sample fluid by means of two turbid signals produced from two different samples whose concentrations are the same, but whose particle diameters are different from each other.

This invention invention contemplates the provision of a densitometer in which a suspension formed of a mixture of liquid, suspended solids and floating matters, which are insoluble with each other, is emusified into a white turbid liquid whose concentration is measured on the basis of turbidity which is changeable in response to a degree of emulsification of the white turbid liquid, comprising:

(a) at least one emulsifier for emulsifying said suspension into two kinds of emulsified states in which said suspension has a large or small particle diameter;

(b) at least one optical cell formed of a transparent substance and continuously passing said suspension after it has been emusified therethrough;

(c) a light source for emitting light which illuminates said suspension;

(d) a light receiving element for detecting that light which has transmitted through said optical cell;

(e) a first calculation circuit for deriving a concentration output by calculation from a first light intensity which has transmitted through said suspension having a small diameter and from a second light intensity which has transmitted through said suspension having a large particle diameter;

(f) a second calculation circuit for further averaging the concentration output from said first calculation circuit.

BRIEF DESCRIPTION OF THE DRAWINGS

A better understanding of the present invention may be had from the following detailed description when read in connection with the accompanying drawings wherein:

FIGS. 3($a$), 3($b$) and 3($c$) are schematic diagrams showing connection and arrangement of circuit elements of the densitometer shown in FIG. 1;

FIG. 6($a$) is a longitudinal sectional view of another embodiment of the densitometer according to the invention, comprising two optical cells connected in parallel;

FIG. 6($b$) is a longitudinal sectional view of a further embodiment of the densitometer according to the invention comprising two optical cells connected in series.

DESCRIPTION OF THE PREFERRED EMBODIMENT

Figure 1:
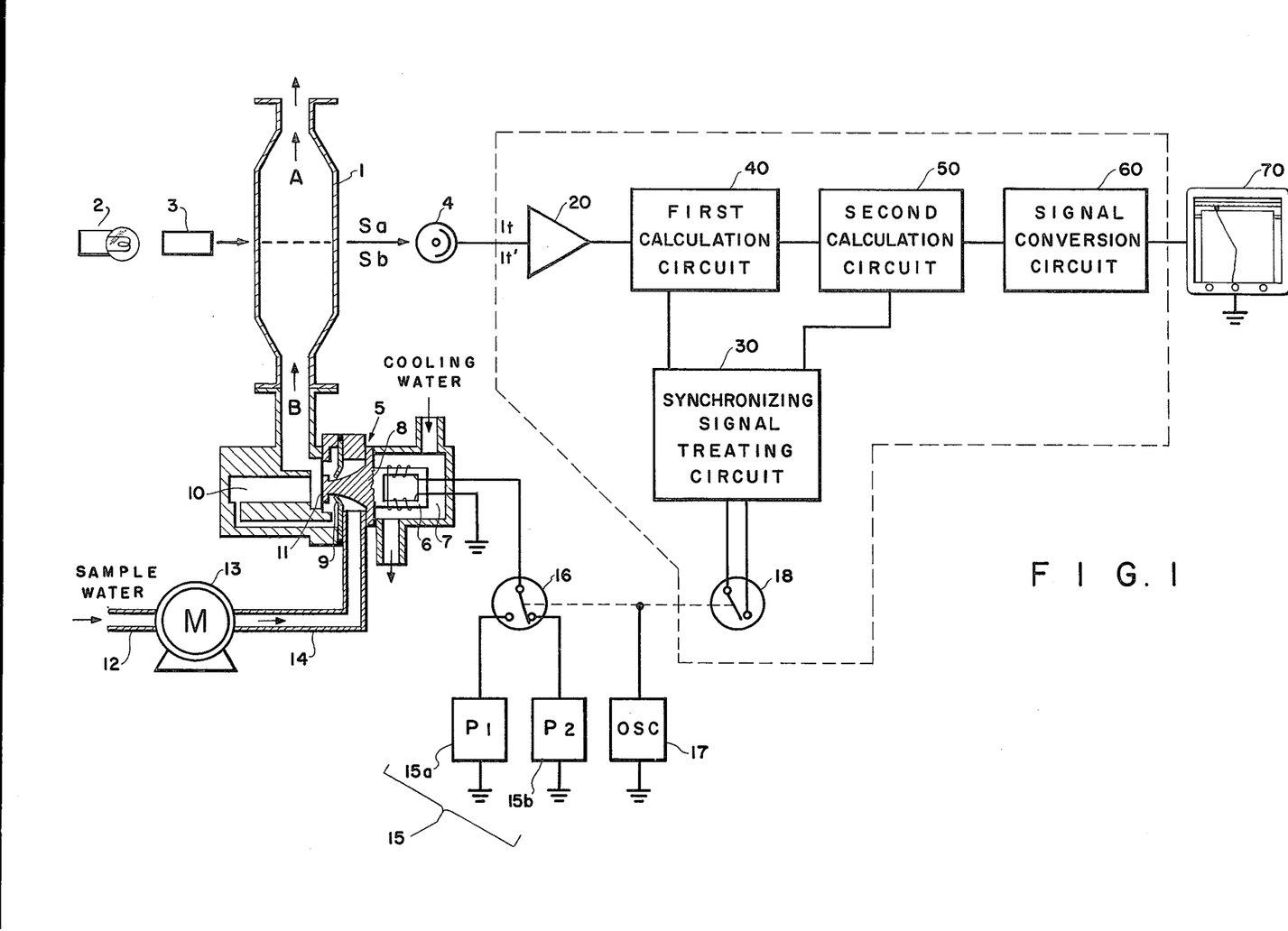
FIG. 1 is a longitudinal sectional view of one embodiment of a densitometer according to the invention illustrating construction and arrangement thereof, partly shown in block diagram.

FIG. 1 shows one embodiment of the densitometer according to the invention for measuring concentration of oil contained in a liquid formed of oil containing exhaust water. Reference numeral 1 designates a cylindrical optical cell formed of a transparent glass through which is passed an emulsified liquid A or B. The sample liquid A contains oil whose particle diameter is small, while the sample liquid B contains oil whose particle diameter is large. Reference numeral 2 shows a light source composed, for example, of a Xenon lamp for emitting monochromatic light. The light emitted from the light source 2 is projected to a collimator 3 which functions to convert the light received into parallel light with which the optical cell 1 is illuminated. The light transmitted through the optical cell 1 filled with a sample liquid is detected by a photoelectric element 4 which may be composed of a photoelectric tube, photocell, cadmium sulfied element, etc. In the present embodiment, the photoelectric element 4 is composed of a photoelectric tube. An emulsifier 5 functions to make the oil contained in the sample liquid uniform in particle diameter and is composed, in the present embodiment, of an ultrasonic wave emulsifier. A high and a low electric power applied to the ultrasonic wave emulsifier 5 causes it to be operated at a constant time difference so as to produce two kinds of sample liquids A and B; sample liquid A containing oil having a small particle diameter and the sample liquid B containing oil having a large particle diameter. The high and low electric powers are supplied to the ultransonic wave emulsifier 5 by periodically coupling a high electric power $P_1$ from a high electric power source 15a and a low electric power $P_2$ from a low electric power source 15b through a change-over switch 16 to the ultrasonic wave emulsifier 5, and by operating the change-over switch 16 in response to an oscillator 17 which repeatedly comes ON or OFF at a constant period. These high and low electric power sources 15a and 15b function to excite a magnetostrictive oscillator 6. The ultrasonic wave emulsifier 5 is provided with a cooling passage 7 through which is supplied a cooling water to the magnetostrictive oscillator 6 for the purpose of preventing the latter from becoming overheated; oscillations produced from the oscilltor 6 are transmitted to a transmitting body 8 which makes contact with liquid mixed with oil and functions to effect primary emulsification. A sample liquid is supplied through a pipe 14 and a gap is formed between an inclined pipe 9 for converging the sample liquid and the transmitting body 8 to a cavity 10 in which the sample liquid is subjected to secondary emulsification and then continuously delivered into the optical cell 1. Between the transmitting body 8 and the cavity 10 is interposed a thin membrane 11 which functions to separate the transmitting body for effecting the primary emulsification of the sample liquid from the cavity 10 for effecting the secondary emulsification thereof.

A pump 13 feeds, at a constant speed, an oil containing liquid taken from a main exhaust pipe for supplying ballast for a tanker, etc. and from a slop tank, etc. (not shown) into a sampling tube 12. The oil containing liquid is then delivered to a pipe 14 connected to the emulsifier 5. As a result, the sample liquid A excited by the high electric power $P_1$ and the sample liquid B excited by the low electric power $P_2$ are alternately passed through the optical cell 1 at a constant period in a continuous manner.

These sample liquids A and B are always illuminated with the monochromatic light and the light transmitted through the optical cell 1 is detected by the photoelectric tube 4 whose output signal is amplified by an amplifier 20 and then supplied to a first calculation circuit 40 to which is supplied a synchronizing signal produced in response to the operation of the change-over switch 16 for changing over the degree of emulsification through a synchronous switch 18 and a synchronizing signal treating circuit 30. The synchronous switch 18 is repeatedly opened and closed at the same period as that of the change-over switch 16; both the synchronous switch 18 and the change-over switch 16 being operated by the output from the oscillator 17. The first calculation circuit 40 functions to effect calculations that logarithmically change the ratio of the two turbid signals based on the degree of emulsification obtained by the high and low electtric powers. This calculation method derives a concentration value in the manner to be described later. This calculation method, however, does not indicate a true concentration of oil in the sample liquid when the concentration of the oil is changing. In order to know the true concentration of the oil, the output from the first calculation circuit 40 is supplied to a second calculation circuit 50 which functions to take an average of the various outputs from the first calculation circuit 40. This calculation operation is treated by the snychronizing signal delivered from the synchronizing signal treating circuit 30 to deliver a concentration output signal which is a close indication of the true concentration. This concentration output is supplied through a signal conversion circuit 60 to a recorder 70 which functions to continuously record the concentration output.

Figure 2:
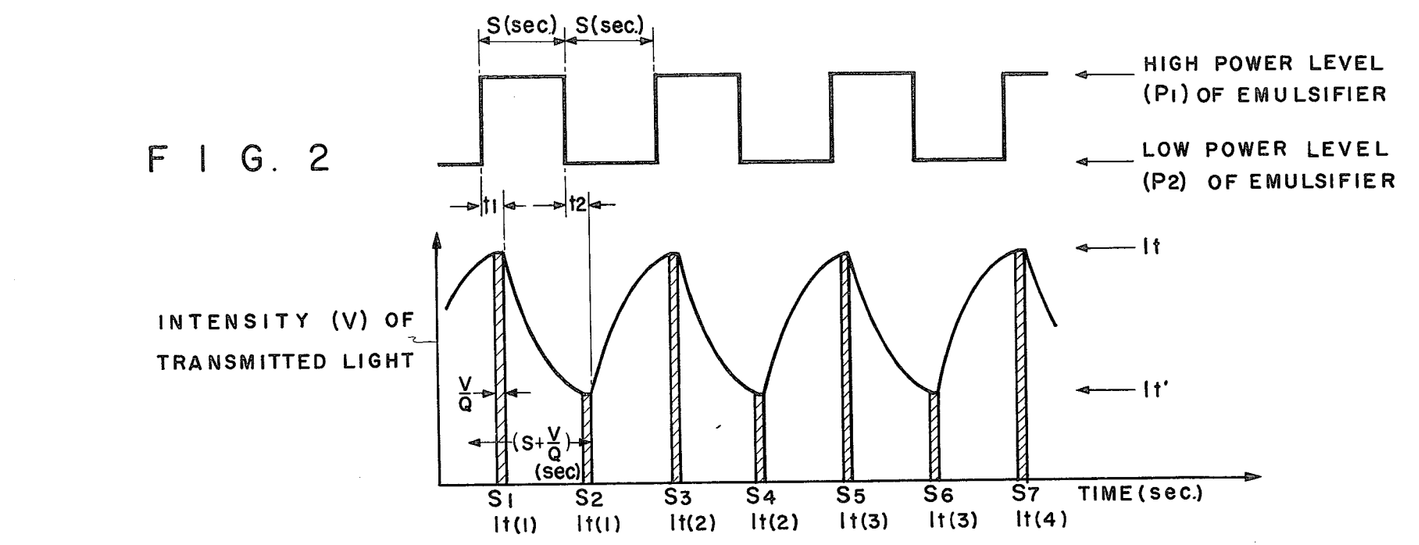
FIG. 2 is characteristic curves for illustrating a principle in operation of the densitometer shown in FIG. 1.
Figure 3A:
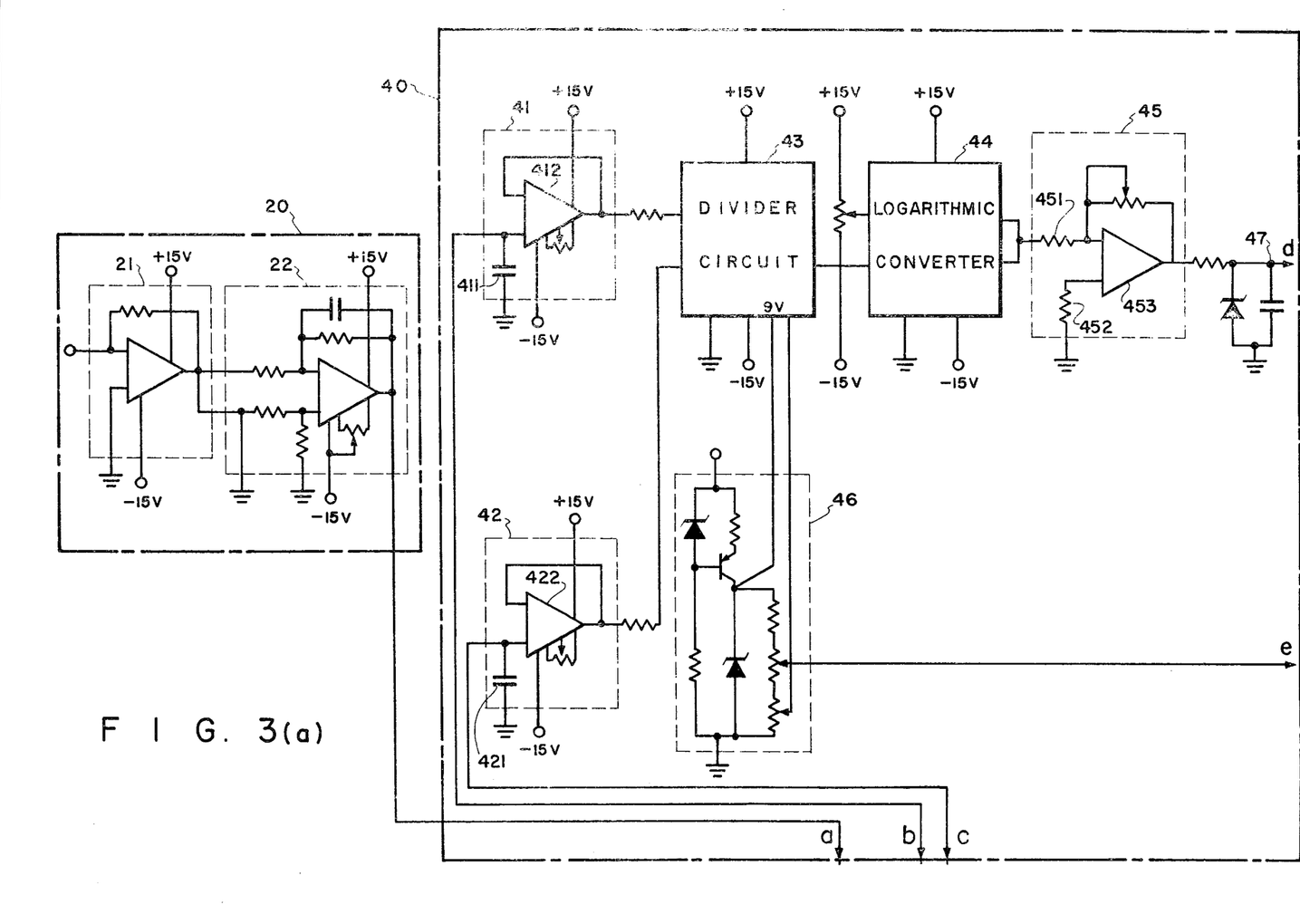
Figure 3B:
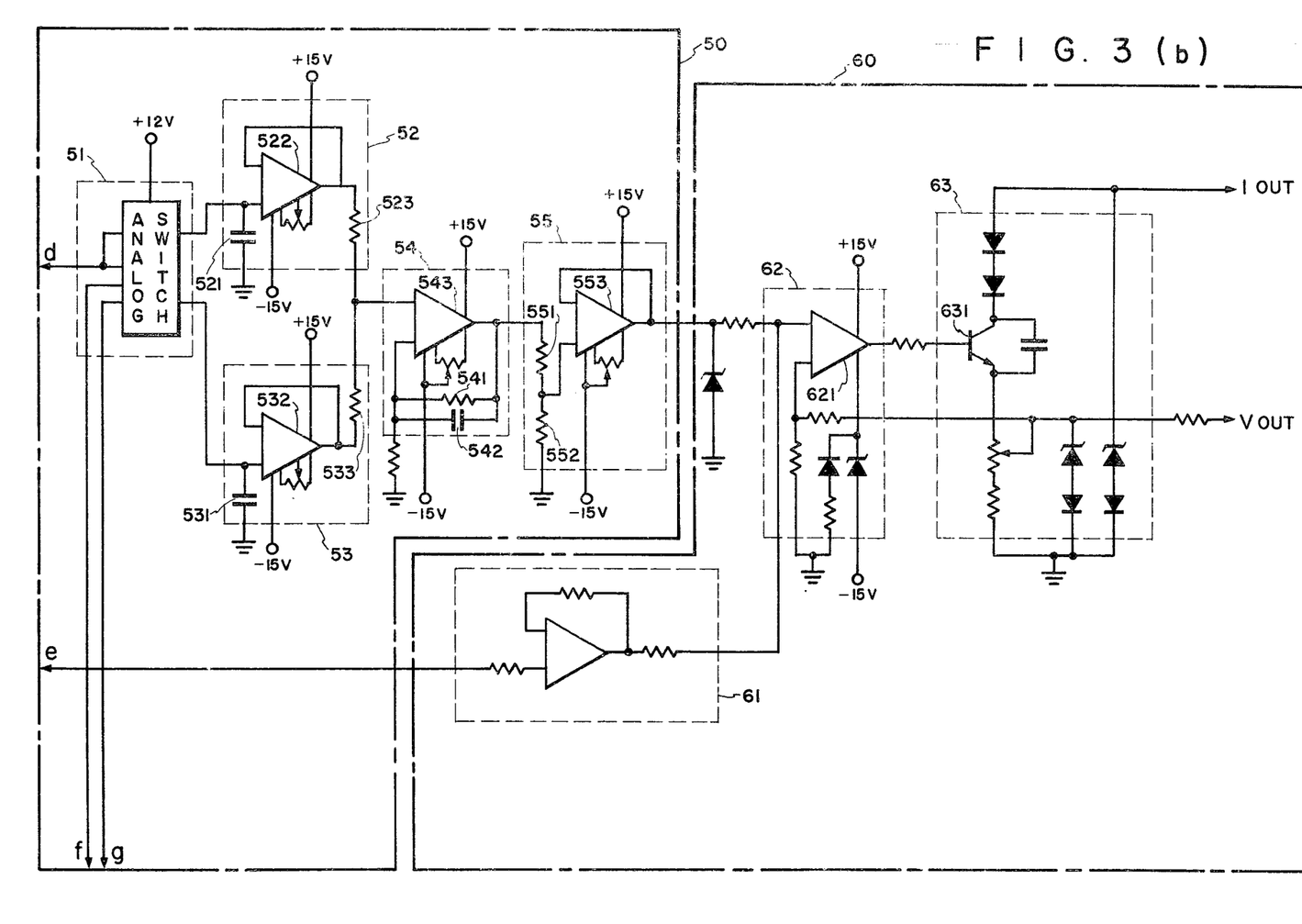
Figure 3C:
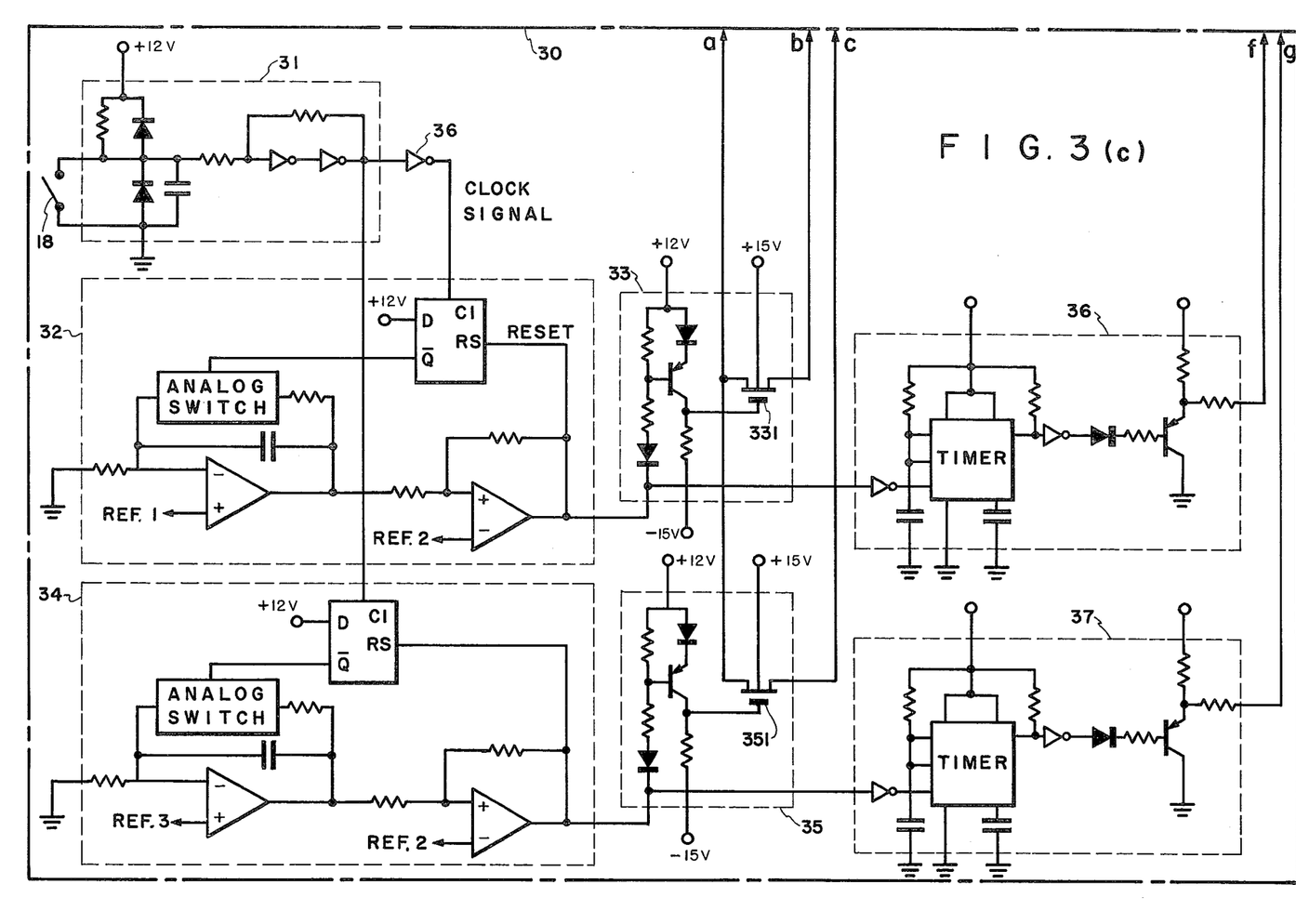

Operation of the present embodiment will now be described with reference to FIGS. 2 and 3. FIG. 2 shows characteristic curves illustrating change of intensity of transmitted light received by the photoelectric tube 4 when the electric power supplied from the electric power source 15 to the emulsifier 5 is changed from the high electric power to the low electric power and vice versa by the change-over switch 16 and the concentration of oil is constant. If an oil containing exhaust liquid delivered by the pump 13 under a constant pressure is excited by the high electric power $P_1$ during a given initial period, the oil particles become divided into finer particles, so that the light illuminating the optical cell 1 is intercepted by a greater amount of particles. As a result, the intensity of transmitted light received by the photoelectric tube 4 after $t_1$ second decreases from a first steady state $It'(1)$ to a next steady state $It(1)$ after a lapse of a short time. The change-over switch 16 is then changed over to supply the low electric power $P_2$ from the electric power source 15 to the emulsifier 5. As a result, the oil particle is dispersed in the exhaust liquid as particles each having a relatively large diameter is compared with the oil particle dispersed in the exhaust liquid when the high electric power $P_1$ is supplied from the electric power source 15 to the emulsifier 5. As a result, after $t_2$ second, the intensity of transmitted light rises and reaches a steady state $It'(2)$ after the lapse of a short time. The time lag $t_1$, $t_2$ exists because of the time required for the oil sample, finely divided by the emulsifier 5, to arrive at a position illuminated with light. Substantially, there is a relation that $t_1 = t_2 (=t)$. The time required for the degree of emulsification produced by the emulsifier 5 to reach a steady state changes in dependence on the amount of flow, piping, etc., and the periods $S_1$ and $S_2$ for changing the electric power source for the emulsifier 5 from the high electric power to the low electric power and vice versa are preset on the basis of these factors.

In the present embodiment, $S_1 = S_2 = S$ is preset for 3 seconds. As a result, even though the true concentration of oil is a given value, in the densitometer for optically measuring the turbidity according to the invention, the turbidity changes in a wave form between I*t* and I*t'* in dependence with the ability of the emulsifier 5.

where the oil concentration is $x$ and the suspended solid concentration is $y$, then from the light scattering theory, the intensities of transmitted light I*t*(x) and I*t'*(t) are given by:

$$It(x) = K \cdot I_o \cdot \eta \cdot 10^{-(\alpha X + \beta y)} \quad (1)$$

$$It'(x) = K' \cdot I_o \cdot \downarrow \cdot 10^{-(\alpha' x + \beta' y)} \quad (2)$$

where $\alpha$ is a proportional coefficient showing an emulsification degree of the sample A; $\alpha'$ is a proportional coefficient showing an emulsification degree of the sample B, K and K' are parameters determined by contamination of the cell and coloring of the sample liquid, $\beta$ and $\beta'$ are proportional coefficients determined by configurations of suspended solid, $\eta$ is a sensitivity of the liqht receiving element, and $I_o$ is the intensity of incident light.

The parameters K and K' are dependent on one optical cell 1 through which is passed the sample liquids A and B. The proportional coefficients $\beta$ and $\beta'$ are determined by the suspended solid and not influenced by the intense or weak operation of the emulsifier 5, per se, so that substantially $K = K'$ and $\beta = \beta'$.

The proportional coefficients $\alpha$ and $\alpha'$ indicate the difference between the emulsifying abilities corresponding to the high electric power $P_1$ and the low electric power $P_2$, so that any change of the electric power level may be effected in accordance with the request in design.

A ratio between the two intensities of transmitted light I*t*(x) and I*t'*(x) can be derived from the equations (1) and (2) and is given by:

$$(It'(x)/It(x)) \approx 10^{(\alpha - \alpha')x}$$

Thus, $$x = (1/\Delta\alpha) \log (It'(x)/It(x)) \quad (3)$$

where $\Delta\alpha = \alpha - \alpha'$.

If the degree of emulsification of oil obtained by the electric power supplied to the emulsifier 5 is determined beforehand, the proportional coefficients of $\alpha$ and $\alpha'$ become known values. That is, as can be seen from the equation (3), if two kinds of samples whose emulsified states are different from each other are prepared and the ratio between the two intensities of transmitted lights I*t*(x) and I*t'*(x) is calculated, the concentration of oil can easily be measured without being influenced by the change of the intensities of light source, coloring of the sample liquid contamination of the cell, fatigue of the light receiving element and suspended solids.

In a specific embodiment of the invention, by way of illustration and not limitation, ballast water containing crude oil is fed to the cell 1 at a rate of about 1.0 liters per minute with a pressure added by pump 13 of about 0.15 to 0.2 kg/cm². The ultrasonic transducer is operated at about 28 KHz with a rated output of the vibrator of 100 watts. The high level power $P_1$ may be on the order of 70 watts causing a vibrating amplitude of about 40 microns and the low power $P_2$ may be 35 watts producing a vibrating amplitude of 20 microns.

The operation of a turbid signal treating circuit will now be described with reference to FIG. 3. As shown in FIG. 1, the turbid signal treating circuit comprises five circuit elements consisting of an amplifier 20, a synchronizing signal treating circuit 30, a first calculation circuit, a second calculation circuit 50 and a signal conversion circuit 60. As shown in FIG. 3(a), the amplifier 20 is composed of an amplifier 21 and a filter 22. The synchronizing signal treating circuit 30 functions to treat the synchronizing signal in such a way that the first calclation circuit 40 is brought into synchronism with the second calculation circuit 50 in the case of changing over the emulsifying power of the ultrasonic wave emulsifier 5. The synchronizing signal produced when the change-over switch 18 is closed is shaped by a shaping circuit 31 and then supplied through an inverter 36 to an I*t* timer circuit 32 and supplied directly to an I*t'* timer circuit 34. The I*t* timer circuit 32 functions to deliver, after the lapse of time S + *t*, a pulse output to both I*t'* gate circuit 33 and one-shot circuit 36. The I*t'* timer circuit 34 functions to deliver, after the lapse of time S + *t*, a pulse output to both I*t'* gate circuit 35 and one-shot circuit 37. The I*t* gate circuit 33 is provided at its output side with an FET gate element 331. The I*t'* gate circuit 35 is provided at its output side with an FET gate element 351. A source terminal of each of the gate elements 331 and 351 is directly coupled to an output of the filter circuit 22. A drain terminal of the gate element 331 is coupled to an I*t* hold circuit 41, while a drain terminal of the gate element 351 coupled to an I*t'* hold circuit 42. The I*t* one-shot circuit 36 and I*t'* one-shot circuit 37 function to delay the outputs from the timer circuits 32 and 34 by a short time of about 50 ms, respectively, and deliver a synchronization change-over signal to the second calculation circuit 50 after a given time delay has been obtained for the purpose of preventing the synchronization change-over signal from being delivered to the input of the second calculation circuit 50 before the output from the first calculation circuit 40 is established. As a result, the output signals from both the I*t* and I*t'* one-shot circuits 36 and 37 are delivered to a switch circuit 51 of the second calculation circuit 50.

The first calculation circuit 40 functions to derive a concentration of a sample such as oil from two turbid signals obtained from the emulsifier 5 as two kinds of intensities of the transmitted lights I*t* and I*t'* whose emulsified states are different from each other. Reference numerals 41 and 42 designate hold circuits for temporarily holding the turbid signal, respectively. The hold circuit 41 is composed of a condenser 411 and a direct current amplifier 412, while the hold circuit 42 is composed of a condenser 421 and an amplifier 422. The turbid signal I*t* produced when the emulsifier 5 is intensely excited is held by the I*t* hold circuit 41, while the turbid signal I*t'* produced when the emulsifier 5 is weakly excited is held by the I*t'* hold circuit 42. After both the turbid signals I*t* and I*t'* have been held by the I*t* and I*t'* hold circuits 41 and 42, respectively, the outputs thereof are delivered to a divider circuit 43 whose output is delivered through a logarithmic converter circuit 44 to a multiplier circuit 45. Reference numeral 46 designates a constant voltage circuit which functions to apply an electric source voltage to the divider circuit 43 and to a bias circuit 61. Both the divider circuit 43 and the logarithmic converter 44 are composed of module elements, respectively, made in U.S.A. by the following companies:

Dividing Module 434B—Analog Device Co.
Logarithmic Conversion Module 755N—Analog Device Co.

The multiplier circuit 45 is composed of resistors 451 and 452 and amplifier 453 and functions to multiply the term 1/Δα in the above equation (3) and bring a concentration scale of 0 to 200 (ppm) into correspondence with voltage 0 to 4 (V).

The second calculation circuit 50 functions to average the concentration signal output from the first calculation circuit 40. The concentration signal output is delivered from the first calculation circuit 40 with an interval of S seconds. In the second calculation circuit 50, a switch circuit 51 functions to supply the concentration signal output to an A hold circuit 52 and then to a B hold circuit 53 so as to cause the A and B hold circuits 52 and 53 to hold the concentration signal output alternately with a time interval of S seconds. Whether the A hold circuit 52 or the B hold circuit 53 functions to hold the concentration signal output is determined by the synchronizing signals from the one-shot circuits 36 and 37 in the synchronizing signal treating circuit 30. The A hold circuit 52 mainly consists of a condenser 521 and a direct current amplifier 522, while the B hold circuit mainly consists of a condenser 531 and a direct current amplifier 532. The outputs from the A and B hold circuits 52 and 53 are supplied through resistors 523 and 533 to the input end of an adder circuit 54. The adder circuit 54 is provided with a feedback circuit composed of a resistor 541 and a condenser 542 and functions as a filter. The output from the adder circuit 54 is divided into halves by means of an attenuator circuit 55 composed of two equal resistors 551, 552 and an amplifier 553.

A signal converter circuit 60 functions to effect such a conversion that the averaged output obtained from the preceding second calculation circuit 50 is adjusted to an input level which corresponds to the characteristics of recorders such as an indicating instrument or any other recorders or the other calculation circuits. The signal converter circuit 60 is composed of an adder circuit 62 and a voltage-to-current converter 63. The adder circuit 62 is provided with a calculation amplifier 621 to which is supplied the output range 0 to 4 (V) from the amplifier 553 and the bias voltage from the bias circuit 61. The output from the adder circuit 62 is supplied to a transistor 631 of the voltage-to-current converter circuit 63 and converted into a spun signal of 4 to 20 MA. As a result, the averaged concentration output is delivered from the calculation amplifier 621 as a voltage output $V_{out}$ and from a collector of the transistor 631 as a current output $I_{out}$.

Figure 5:
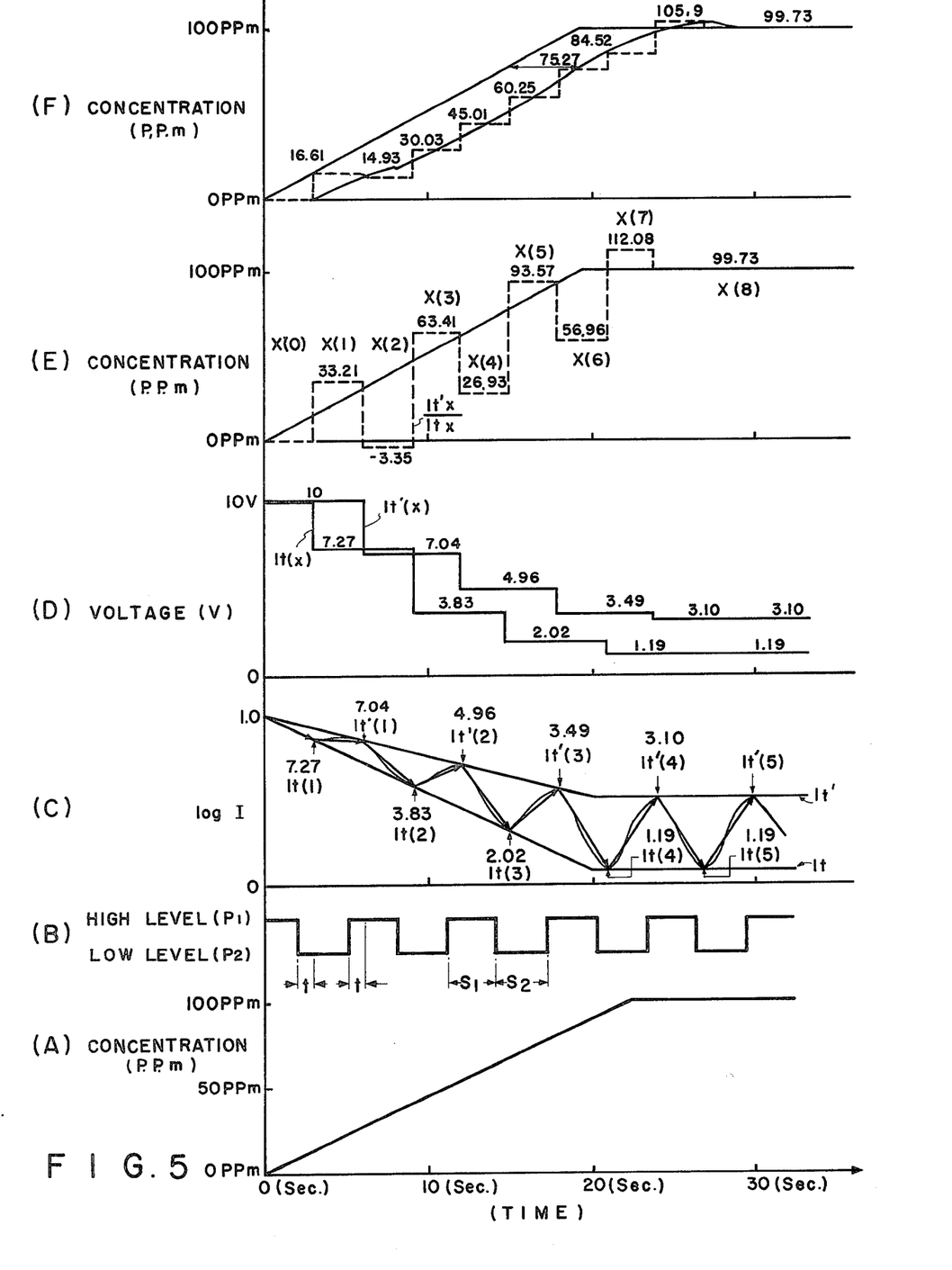
FIG. 5 shows characteristic curves illustrating the operational condition of the densitometer shown in FIG. 1.

The operation of the turbid signal treating circuit 50 constructed and arranged as described above will now be described with reference to FIG. 5. For ease of understanding, a parameter K, a sensitivity η and a light intensity $I_o$ in the operation of FIG. 5 are assumed to be, respectively, $K = 1$, $\eta = 1$ and $I_o = 10$. FIg. 5 shows characteristic curves of various parts of the turbid signal treating circuits shown in FIG. 3 when the concentration of the sample liquid is changed in function of time as shown in FIG. 5(A). In FIG. 5(B) is shown a voltage change applied to the emulsifier 5 in response to the operation of the change-over switch 16. This change-over signal is detected as the synchronizing signal by the switch 18. The synchronizing signal is then supplied through the pulse shaping circuit 31 to the inverter 36. The pulse shaping circuit 31 and the inverter 36 function to separate the synchronizing signal into two signals whose phases are different from each other by 180°. These two signals are applied to timer circuits 32 and 34, respectively. After the lapse of S + t (seconds), pulses are supplied from the timer circuit 32 and 34 to the gate circuits 33 and 35 and the one-shot circuits 36 and 37, respectively. The gate circuits 33 and 35 function to open gates of the FET 331, 351 for about 10 ms to make its source-to-drain path conductive. The timer circuits 32 and 34 receive the signals whose phases are different from each other by 180°, so that when the timer circuit 32 is operative the timer circuit 34 becomes inoperative and when the timer circuit 34 is operative the timer circuit 32 becomes inoperative. As a result, the timer circuits 32 and 34 repeatedly become operative and inoperative every S seconds. The gate circuits 33 and 35 operate in the same manner. The FET 331 and and the FET 351 become alternately conductive with a time interval of about 10 ms every S seconds.

If the emulsifying power of the emulsifier 5 is changed under such condition that the concentration of the sample liquid is increased for a moment, a photoelectric current having a waveform shown in FIG. 5(C) flows through the photoelectric tube 4. In FIG. 5(C), an envelope It' shows a receiving light intensity characteristic when the emulsifier 5 is excited by the low electric power and an envelope It shows a receiving light intensity characteristic when the emulsifier 5 is excited by the high electric power.

The wave-shaped measured amount is further amplified by the preamplifier 21. If the high electric were power excitation of the emulsifier 5 is changed over to the low electric power excitation after the lapse of lapping time t, the peak value It(1) of the concentration the sample liquid when the emulsifier 5 is excited by the high electric power is measured by the photoelectric tube 4. Then, the FET 331 becomes instantaneously conductive and the peak value It(1) is held by the condenser 411 of the It hold circuit 41. Subsequently, since the emulsifier 5 is excited by the low electric power, the receiving light intensity approaches to the envelope It'. After the lapse of S seconds, the receiving light intensity substantially reaches to the envelope It'. At this time, the FET 351 becomes instantaneously conductive and the peak value It'(1) is held by the condenser 421 of the It' hold circuit 42. Then, the emulsifier 5 is excited again by the high electric power, so that the receiving light intensity approaches to the envelope It and the FET 331 becomes conductive again; and, as a result, the peak value It(2) is held. These operations will be repeated in the similar manner. As shown in FIG. 5(D), the It hold circuit 41 functions to effect sampling of peak values of It(1), It(2), It(3) . . . every 2S seconds and the It' hold circuit 42 functions to hold peak values of It'(1), It'(2), It'(3) . . . .

Outputs from the hold circuits 41 and 42 are delivered through the divider circuit 43 and the logarithmic converter circuit 44 to the multiplier circuit 45. As a result, at the output end 47 of the first calculation circuit 40 is calculated the oil concentration x obtained by the above treatment in function of the time interval of S seconds as shown in FIG. 5 (E).

$$x(0) = 0, \; x(1) = \frac{1}{\Delta\alpha} \log \frac{10}{It(1)}, \; x(2) = \frac{1}{\Delta\alpha} \log \frac{It'(1)}{It(1)}, \quad (4)$$

$$x(3) = \frac{1}{\Delta\alpha} \log \frac{It'(1)}{It(2)}, \; x(4) = \frac{1}{\Delta\alpha} \log \frac{It'(2)}{It(2)}$$

$$x(5) = \frac{1}{\Delta\alpha} \log \frac{It'(2)}{It(3)}, \; x(6) \ldots$$

FIG. 5(E) substantially shows the concentration of the sample liquid. This result is always responsive to a rectangular wave form with respect to the change of concentration. In addition, rapid and steep changes result in a rectangular wave form having a large amplitude, so that it is difficult to discriminate a true concentration. In the case of measuring a slowly changeable concentration of a sample liquid, the output from the first calculation part 40 may be delivered through the signal conversion circuit 60 without passing through the second calculation circuit 50 to the indicating instrument 70 which indicates and records the concentration being measured. In the case of measuring a rapidly and steeply changeable concentration of a sample liquid, the output from the first calculation circuit 40 is delivered to the second calculation circuit 50 which functions to average the concentration signal produced by the first calculation circuit 40 and having the rectangular wave form. In addition, the filter characteristic of the adder 54 serves to correctly derive a concentration signal which corresponds to the true concentration in a straight line manner.

That is, the switch circuit 51 of the second calculation circuit 50 functions to alternately deliver the output from the first calculation part 40 every S seconds by means of the synchronizing signal alternately delivered with a time difference of S seconds from the one-shot circuits 36 and 37 of the synchronizing signal treating circuit 30. In this case, the gate pulse of the gate circuits 33 and 35 is about 10 ms and the output pulse from the one-shot circuits 36 and 37 is on the order of about 50 ms. These gate pulses and output pulses are simultaneously raised and delivered to the first and second calculation circuits 40 and 50, respectively. As a result, the oil concentrations $x$ given by the above-mentioned equation (4) are held to each of the A and B hold circuits 52 and 53 of the second calculation circuit 50 every 2S seconds as follows:

A hold circuit 52 → $x(0), x(2), x(4), x(6) \ldots$
B hold circuit 53 → $x(1), x(3), x(5), x(7) \ldots$ In the succeeding adder circuit 54, the two outputs from the A and B hold circuits 52 and 53 are added with each other. In this case, the output end of the adder circuit 54 is fed back through the resistor 541 and the condenser 542 to the inverted input end of the amplifier 543, so that the adder circuit 54 functions as a filter having a time constant $\tau$ which is equal to about 3 seconds. The output from the adder circuit 54 is supplied to the resistors 551 and 552 of the attenuater circuit 55 and divided into approximate halves and then supplied to the calculation amplifier 553 thus completing the averaging operation of the second calculation circuit 50. Such averaging operation causes the output pulses from the second calculation circuit 50 to follow the rapid changes of the oil concentration as shown in FIG. 5(F). In addition, since the adder circuit 54 functions as a filter circuit, it is possible to indicate substantially true oil concentration.

In order to adapt the output from the first and second calculation circuits 40, 50 to the design of the indicating instrument, to an adder circuit 62 of the signal converter, circuit 60 is added a given voltage from the bias circuit 61 and the voltage-to-current converter circuit 63 functions to convert it into the current output $I_{out}$.

Figure 4:
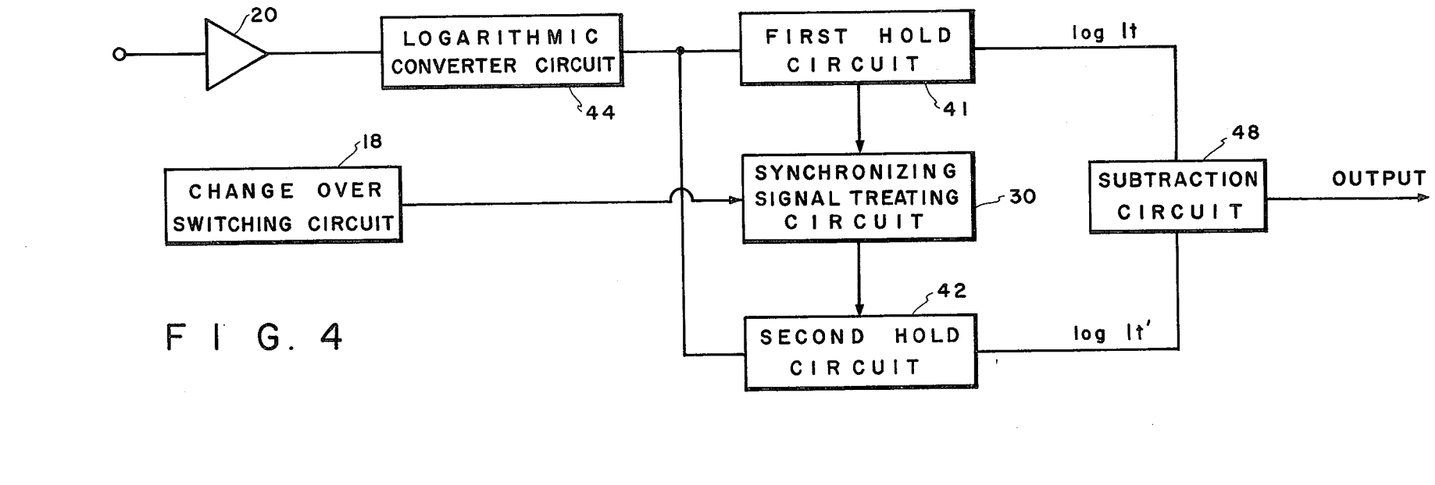
FIG. 4 is a block diagram showing modified connection and arrangement of the first calculation circuit shown in FIG. 3($a$)

In the above-described operation of the turbid/concentration signal treating circuit, the various kinds of circuit arrangements may be modified without changing their abilities. For example, in FIG. 4 is shown another embodiment of the first calculation circuit 40 shown in FIG. 1. The output from the photoelectric tube 4 is supplied through the amplifier 20 to the logarithmic converter circuit 44 which functions to convert the input thereof into a logarithmic value. The synchronizing signal treating circuit 30 is operated in response to the operation of the change-over switch 18 to control the I$t$ hold circuit 41 so as to hold the log I$t$ therein and control the I$t'$ hold circuit 42 so as to hold the log I$'$ therein. Subsequently, both the log I$t$ and the log I$t'$ are delivered to a subtraction circuit 48 which is on the market as an analog element, and the output of the circuit 48 may be supplied to the second calculation circuit 50. In this way, the circuit arrangement shown in FIG. 4 functions in the same manner as the first calculation circuit 40. Such a circuit in FIG. 4 can be easily realized by those skilled in the art with reference to the system of FIG. 3(a), and the concrete arrangement of this circuit is omitted.

Figure 6A:
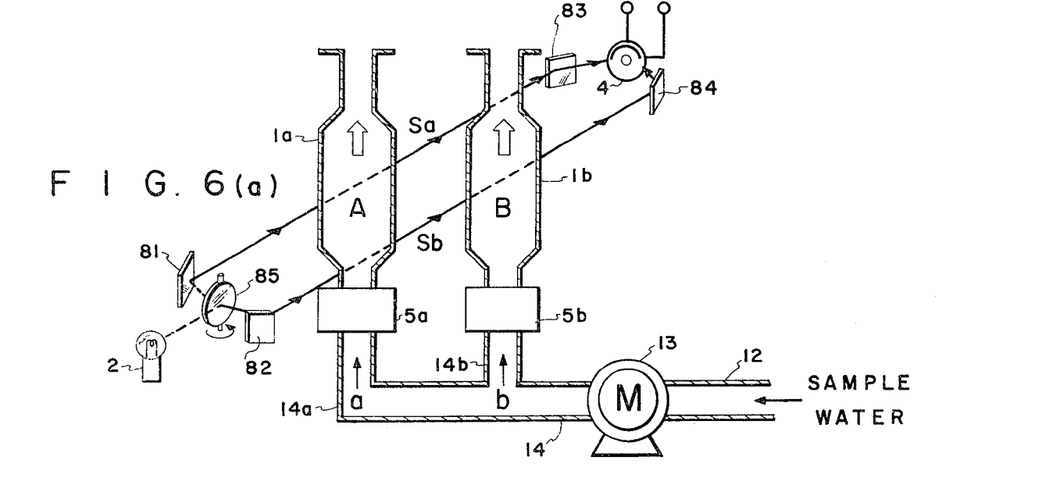
Figure 6B:
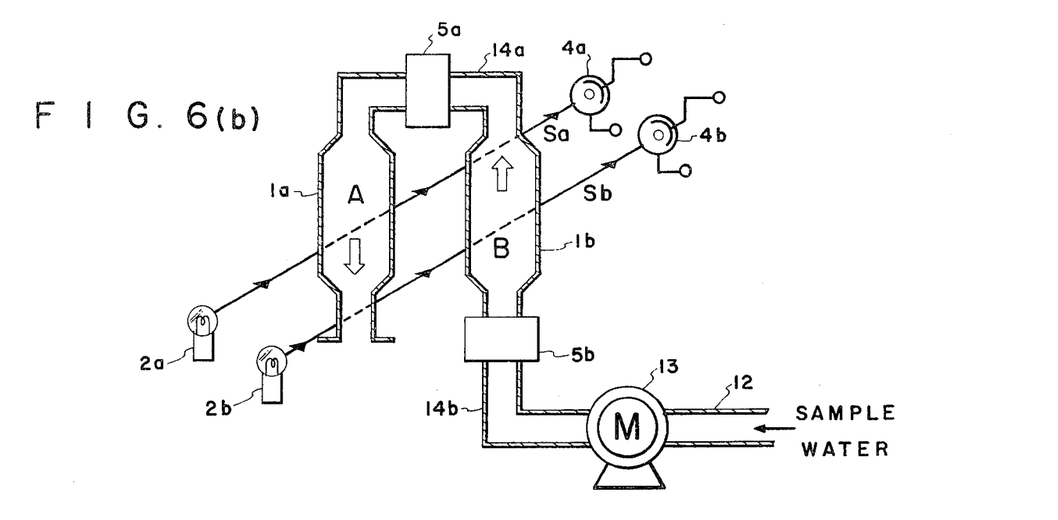

In FIG. 6 is shown two modified embodiments of the optical cell shown in FIG. 1. In FIG. 6(a) is shown two optical cells connected in parallel and in FIG. 6(b) is shown two optical cells connected in series.

In the embodiment shown in FIG. 6(a), both the optical cells 1a and 1b are provided at their branch pipes 14a and 14b with emulsifiers 5a and 5b, respectively, which are different in their emulsifying powers from each other. These branch pipes 14a and 14b are communicated in common with the pipe 14. Transmitted lights S$a$ and S$b$ passed through the emulsified sample liquids A and B are measured by an optical system. In the optical system, light emitted from the light source 2 is reflected by a rotary mirror 85 into two lights which are reflected by two fixed mirrors 81 and 82 and transferred to the optical cells 1a and 1b, respectively. The lights transmitted through the optical cells 1a and 1b are incident on and reflected by other fixed mixed mirrors 83 and 84 and then projected onto the photoelectric tube 4 which functions to detect two kinds of transmitted lights S$a$ and S$b$. In the present embodiment, the first and second calculation circuits 40 and 50 are controlled by synchronizing signals obtained from the rotary mirror 85. If the rotary mirror 85 is rotated at a high speed, it is possible to omit the second calculation circuit 50 which functions to take an average of the various outputs from the first calculation circuit 40.

In FIG. 6(b) showing the two optical cells 1a and 1b connected in series, all of the emulsifier 5a, optical cell 1a, emulsifier 5b and optical cell 1b are connected in series. The optical cells 1a and 1b are arranged side by side and in parallel with each other. Lights emitted from two light sources 2a and 2b are projected onto the optical cells 1a and 1b, respectively, and the transmitted light S$a$ and S$b$ through the optical cells 1a and 1b are incident on photoelectric tubes 4a and 4b, respectively, which function individually to detect changes of the turbidity of the sample liquid. The light measuring device which makes use of the two light sources 2a and 2b and the two light receiving elements 4a and 4b can detect the turbidity of the sample liquid in the two optical cells 1a and 1b continuously, so that it is possible to use a calculation circuit which is extremely simple in construction.

Figure 7:
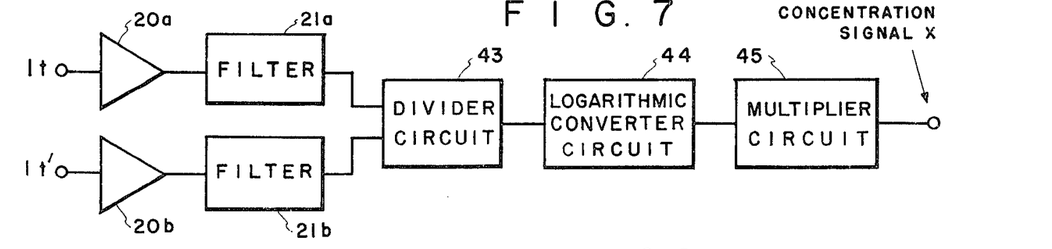
FIG. 7 is a block diagram showing one embodiment of a turbid signal treating circuit for the densitometer comprising two optical cells shown in FIG. 6($b$).

In FIG. 7 is shown a calculation circuit for the light measuring device using two light receiving elements 4a and 4b shown in FIG. 6(b). The transmitted light intensities $I_t$ and $I_t'$ detected by the photoelectric tubes 4a and 4b are supplied through preamplifiers 20a and 20b and filters 21a and 21b to the divider circuit 43 without passing through the $I_t$ and $I_t'$ hold circuits and then supplied through the logarithmic converter circuit 44 to the multiplier circuit 45 which functions to adjust the output thereof thus deriving the concentration signal x. Applying the system of FIG. 3(a), a concrete circuit arrangement (not shown) of FIG. 6(b) is well understood by those skilled in the art.

As can be seen from the above, the embodiments shown in FIGS. 6(a) and 6(b) provide a light measuring device which can eliminate the time lag as shown in FIG. 5(F) and which has a rapid response property.

The optical system and the sampling device shown in FIG. 6 may be combined in any suitable manner without departing from the technical scope of the invention.

The embodiments of the invention in which an exclusive property or privilege is claimed are defined as follows:

1. A densitometer for measuring a concentration of a liquid in a system including liquids and suspended solids insoluble in each other, comprising in combination:
   means for producing two emulsified conditions of the system, a first condition containing an emulsified liquid of relatively large particle diameter and a second condition containing an emulsified liquid of a relatively small particle diameter;
   means for illumination;
   means for receiving light from said illuminating means and producing an electrical signal proportional to the quantity of light received;
   means for containing said system, said containing means disposed between said illuminating means and said light receiving means;
   said light receiving means generating a first signal in response to the light passing through said system in said first condition and a second signal in response to the light passing through said system in said second condition; and
   means responsive to said first signal and said second signal for generating a signal proportional to the concentration of said emulsified liquid.

2. A densitometer for measuring a concentration of a liquid in a system including liquids and suspended solids insoluble in each other, comprising in combination:
   at least one emulsifier for emulsifying said system into two emulsified states, one state in which said liquid has a relatively large particle diameter and another state in which said liquid has a relatively small particle diameter;
   at least one optical cell, said system passing through said cell after it has been emulsified;
   at least one light source for emitting light which illuminates said system in said cell;
   at least one light receiving element for detecting that light which has transmitted through said optical cell; and
   a calculation circuit for producing an output signal proportional to the concentration of one of said liquids from a first electric signal obtained from said light receiving element as said system passes through said cell in said emulsified state having a small particle diameter and from a second electric signal obtained from said light receiving element as said system passes through said cell in said emulsified state having a large particle diameter.

3. A densitometer for measuring a concentration of a liquid in a system including liquids and suspended solids insoluble in each other, comprising in combination:
   an emulsifier for continuously emulsifying a system into two emulsified conditions, a first condition containing suspended matter having a relatively large particle diameter and a second condition containing a suspended matter having a relatively small particle diameter;
   a photometric cell formed of a transparent substance and connected to an outlet side of said emulsifier so as to continuously pass the sample water emulsified through said photometric cell;
   a light source for illuminating said system as it passes through said cell;
   a light receiving and photoelectric conversion element for generating a first and a second turbid signal in response to light penetrating through said system in first and second conditions, respectively; and
   a calculation circuit for removing a common signal component from first and second turbid signals and for driving a signal corresponding to the concentration of a liquid in said system.

4. A densitometer according to claim 3 wherein said calculation circuit includes means for deriving a ratio of said first turbid signal and said second turbid signal and a circuit for logarithmically converting an output signal from said ratio means.

5. A densitometer according to claim 3 wherein said calculation circuit includes a circuit for logarithmically converting said first and second turbid signals, respectively, and means for effecting subtraction of said first and second electric signals converted by said circuit, said logarithmic circuit and said subtraction means removing a signal component due to said suspended solids.

6. A densitometer for measuring a concentration of a liquid in a system including liquids and suspended solids insoluble in each other, comprising in combination:
   an ultrasonic emulsifier for continuously emulsifying said system and capable of alternating its ultrasonic excitation between a first and second state so as to produce two emulsified conditions, a first condition containing an emulsified liquid having a relatively large particle diameter and a second condition containing an emulsified liquid having a relatively small particle diameter;
   means for alternating between said first and second excitation capability for predetermined intervals;
   one photometric cell formed of a transparent substance and connected to an outlet side of said emulsifier so as to alternately pass system in said first and second conditions through said photometric cell;
   a light source for illuminating said cell;
   a photoelectric conversion element for detecting light passing through said cell and for producing first and second turbid signals in response to said system in said first and second conditions, respectively;
   a first calculation circuit for removing a signal component due to said solid matter from first and second turbid signals, respectively, and deriving a signal corresponding to the concentration of said liquid; and
   means for synchronizing with said alternating means for sampling said first or second electric signal after a lapse of a given time from the change of said excitation.

7. A densitometer for measuring a concentration of a liquid in a system including liquids and suspended solids insoluble in each other, comprising in combination:
an ultrasonic emulsifier for continuously emulsifying said system and capable of alternating its ultrasonic excitation between a first and second state so as to produce two emulsified conditions, a first condition containing an emulsified liquid having a relatively large particle diameter and a second condition containing an emulsified liquid having a relatively small particle diameter;
means for alternating between said first and second excitation capability for predetermined intervals;
one photometric cell formed of a transparent substance and connected to an outlet side of said emulsifier so as to alternately pass system in said first and second conditions through said photometric cell;
a light source for illuminating said cell;
a photoelectric conversion element for detecting light passing through said cell and for producing first and second turbid signals in response to said system in said first and second conditions, respectively;
a first calculation circuit for removing a signal component due to said solid matter from first and second turbid signals, respectively, and deriving a signal corresponding to the concentration of said liquid;
means for synchronizing with said alternating means for sampling said first or second electric signal after a lapse of a given time from the change of said excitation; and
a second calculation circuit including means for averaging maximum and minimum values of a signal derived from said first calculation circuit corresponding to the concentration of said liquid.

8. A densitometer according to claim 7 and further comprising a circuit for bringing the averaging calculation of said second calculation circuit into synchronism with the alternating means to effect the averaging calculation in every predetermined period.

9. A densitometer according to claim 8 and further comprising a filter means for smoothing the concentration signal synchronized and averaged.

10. A densitometer for measuring a concentration of a liquid in a system including liquids and suspended solids insoluble in each other, comprising in combination:
an emulsifying apparatus composed of a first emulsifier for producing a first emulsion containing a suspended matter having a large particle diameter and a second emulsifier for producing a second emulsion containing a suspended matter having a small particle diameter;
a photometric cell apparatus formed of a transparent substance and composed of a first photometric cell through which is passed said first emulsion and a second photometric cell through which is passed second second emulsion;
two light sources for independently illuminating said first and second emulsion in said cells, respectively;
two photoelectric elements for generating first and second turbid signals from light penetrating through said first and second emulsions, respectively; and
a first calculation circuit for removing a signal component due to solids from first and second electric signals obtained from said first and second turbid signals, respectively, and deriving a signal corresponding to the concentration of said liquid.

11. A densitometer according to claim 10 wherein a joint body composed of said first emulsifier and said first photometric cell is connected in parallel with a joint body composed of said second emulsifier and said second photometric cell.

12. A densitometer according to claim 10 wherein a joint body composed of said first emulsifier and said first photometric cell is connected in series with a joint body composed of said second emulsifier and said second photometric cell.

13. A densitometer for measuring a concentration of a liquid in a system including liquids and suspended solids insoluble in each other, comprising in combination:
an emulsifying apparatus composed of a first emulsifier for producing a first emulsion containing a suspended matter having a large particle diameter and a second emulsifier for producing a second emulsion containing a suspended matter having a small particle diameter;
a photometric cell apparatus formed of a transparent substance and composed of a first photometric cell through which is passed said first emulsion and a second photometric cell through which is passed said second emulsion;
one light source for alternately illuminating said first and second emulsions in said cells through a rotary mirror;
means for concentrating light penetrated through said emulsion onto a photoelectric conversion element which operates a first and a second turbid signal;
a synchronization means for sampling said first and second turbid signals in synchronism with a rotating period of said rotary mirror;
a first calculation circuit for removing a signal component due to solids from said first and second turbid signals, respectively, and deriving a signal corresponding to the concentration liquid; and
a second calculation circuit including means for averaging maximum and minimum values of a signal derived from said first calculation circuit corresponding to the concentration of said suspension matter.

* * * * *